(12) United States Patent
Bizup et al.

(10) Patent No.: US 8,696,647 B2
(45) Date of Patent: Apr. 15, 2014

(54) CATHETER-TO-DEVICE LOCKING SYSTEM

(75) Inventors: Raymond Bizup, Feasterville, PA (US);
Mark S. Fisher, Sellersville, PA (US)

(73) Assignee: Medical Components, Inc.,
Harleysville, PA (US)

( * ) Notice: Subject to any disclaimer, the term of this patent is extended or adjusted under 35 U.S.C. 154(b) by 794 days.

(21) Appl. No.: 12/142,657

(22) Filed: Jun. 19, 2008

(65) Prior Publication Data

US 2008/0319421 A1 Dec. 25, 2008

Related U.S. Application Data

(60) Provisional application No. 60/936,259, filed on Jun. 19, 2007.

(51) Int. Cl.
*A61M 25/18* (2006.01)
(52) U.S. Cl.
USPC .......................................................... 604/535
(58) Field of Classification Search
USPC ............... 604/103, 165.01, 165.02, 533–538, 604/905; 285/242, 243, 256
See application file for complete search history.

(56) References Cited

U.S. PATENT DOCUMENTS

| | | | |
|---|---|---|---|
| 3,456,965 A | 7/1969 | Gajewski et al. |
| 4,405,163 A | 9/1983 | Voges et al. |
| 4,704,103 A | 11/1987 | Stober et al. |
| 4,723,948 A | 2/1988 | Clark et al. |
| 4,744,788 A | 5/1988 | Mercer |
| 4,762,517 A | 8/1988 | McIntyre et al. |
| 4,778,452 A | 10/1988 | Moden et al. |
| 4,929,236 A | 5/1990 | Sampson |
| 5,185,003 A | 2/1993 | Brethauer |
| 5,213,574 A | 5/1993 | Tucker |
| 5,360,407 A | 11/1994 | Leonard |
| 5,399,168 A | 3/1995 | Wadsworth, Jr. et al. |
| 5,637,102 A | 6/1997 | Tolkoff et al. |

(Continued)

FOREIGN PATENT DOCUMENTS

| | | |
|---|---|---|
| EP | 0976418 B1 | 10/2004 |
| FR | 2703593 A1 | 4/1993 |

(Continued)

OTHER PUBLICATIONS

"stem." Compact Oxford English Dictionary. 2009. AskOxford. <http://www.askoxford.com/concise_oed/stem_1?view=uk>.*

(Continued)

*Primary Examiner* — Kami A Bosworth
(74) *Attorney, Agent, or Firm* — Blank Rome LLP

(57) ABSTRACT

A locking component (100,200,300,400) for locking a catheter proximal end onto a stem (16,56) of a medical device. The locking component has upper and lower parts (104,102; 204,202) that self-secure to each other, preferably in a first position partially open but still assembled, and a second position, locked fully together. The locking component has a compression surface (106,206) to compress the catheter lumen wall against the stem at a location axially offset from the protuberance(s) along the stem of the medical device. A method is disclosed for mechanically securing a catheter to a medical device that can involve placing the pre-assembled locking component along the catheter prior to securing the proximal catheter end to the stem of the medical device and then moving the locking component into position around the stem and then pressing it together into its second locked position, compressing the catheter lumen wall against the stem.

15 Claims, 6 Drawing Sheets

(56) References Cited

U.S. PATENT DOCUMENTS

| | | |
|---|---|---|
| 5,833,654 A | 11/1998 | Powers et al. |
| 5,848,989 A | 12/1998 | Vallani |
| 6,003,906 A * | 12/1999 | Fogarty et al. ............... 285/242 |
| 6,113,572 A | 9/2000 | Gailey et al. |
| 6,155,610 A * | 12/2000 | Godeau et al. ............... 285/242 |
| 6,221,064 B1 | 4/2001 | Nadal |
| 6,971,390 B1 | 12/2005 | Vasek et al. |
| 6,976,980 B2 * | 12/2005 | Brenner et al. ............... 604/535 |
| 2004/0111056 A1 | 6/2004 | Weststrate et al. |
| 2004/0181209 A1 | 9/2004 | Gross |
| 2005/0085794 A1 | 4/2005 | Denoth et al. |
| 2005/0251102 A1 | 11/2005 | Hegland et al. |
| 2007/0219510 A1 | 9/2007 | Zinn et al. |
| 2007/0270770 A1 | 11/2007 | Bizup |
| 2007/0276356 A1 | 11/2007 | Downing et al. |
| 2008/0097296 A1 * | 4/2008 | Pepin ............................ 604/103 |

FOREIGN PATENT DOCUMENTS

| | | |
|---|---|---|
| FR | 2703593 A1 | 10/1994 |
| FR | 2776747 A1 | 10/1999 |
| SE | 463116 B | 8/1990 |
| WO | WO/2004/002555 | 1/2004 |
| WO | 2006/004943 A2 | 1/2006 |

OTHER PUBLICATIONS

International Search Report dated Sep. 5, 2008; PCT/US2008/067527 (5 pages).

Brochure, "R•Port Implantable Vascular Access System Instructions for Use"; Therex Corporation (1994) (8 pages).

PCT/US2008/067515, International Preliminary Report on Patentability dated Dec. 22, 2009, 9 pages.

PCT/US2008/067515, International Search Report dated Sep. 5, 2008, 3 pages.

PCT/US2008/067515, Response dated Apr. 7, 2010, 28 pages.

PCT/US2008/067515, Written Opinion dated Dec. 19, 2009, 8 pages.

PCT/US2008/067527, International Preliminary Report on Patentability dated Apr. 13, 2011, 6 pages.

PCT/US2008/067527, Written Opinion dated Dec. 19, 2009, 8 pages.

* cited by examiner

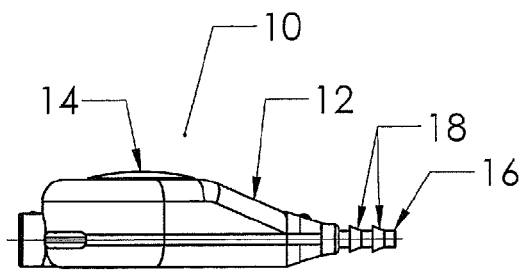
Fig. 1 PRIOR ART
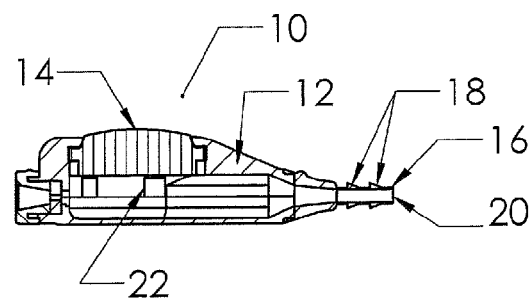
Fig. 2 PRIOR ART
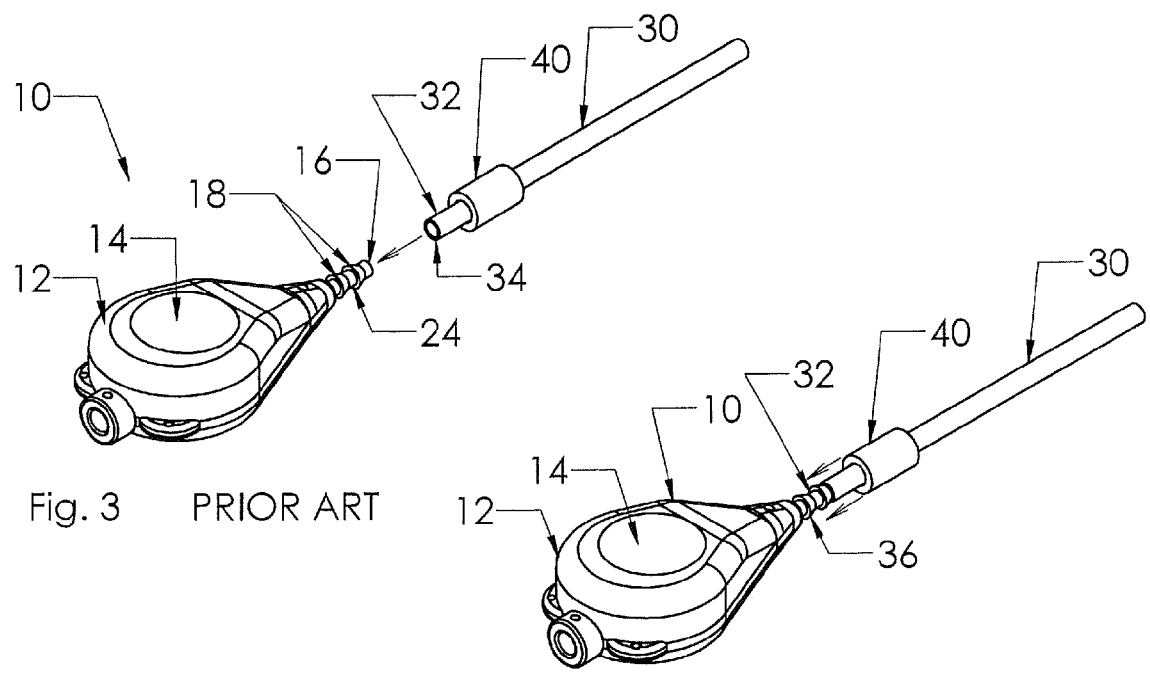
Fig. 3 PRIOR ART
Fig. 4 PRIOR ART

CATHETER-TO-DEVICE LOCKING SYSTEM

CROSS-REFERENCE TO RELATED APPLICATIONS

This application claims priority from U.S. Provisional Patent Application Ser. No. 60/936,259 filed Jun. 19, 2007.

FIELD OF THE INVENTION

This relates to the field of medical devices and more particularly to catheter assemblies and ports therefor, for the infusion of fluids into the patient and withdrawal of fluids from the patient.

BACKGROUND OF THE INVENTION

Infusion ports for the infusion and/or withdrawal of fluids from a patient are well-known, secured to the proximal end of an implanted catheter. These ports are typically used for drug infusion or small amounts of blood withdrawal, where large flows of fluid are not required. The ports are assemblies of a housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574; 5,637,102 and 6,113,572.

United States Patent Publication No. US 2007/0219510, partially assigned to the assignee hereof, discloses a venous access port having a needle-impenetrable housing and a needle-penetrable septum enabling infusion of fluid into the port, providing an interior reservoir and a passageway extending from the reservoir through a stem of a discharge port to establish fluid communication with a proximal end of a catheter lumen to which the port assembly is secured prior to placement of the assembly into a patient. The discharge port is defined by a discharge stem extending from the port assembly and is adapted to be inserted into the lumen of the proximal end of a catheter that extends into the vasculature of the patient. The discharge stem defines a pair of barbed protuberances onto which the catheter lumen wall grips tightly when the stem is fully inserted into the catheter proximal end. This is seen in FIGS. 1 to 4 hereof. FIGS. 3 and 4 depict generally the procedure of locking a catheter proximal end onto the discharge stem using a locking sleeve.

United States Patent Publication No. US 2007/0270770, assigned to the assignee hereof, discloses a venous access port having a housing and a septum, providing an interior reservoir and a passageway extending from the reservoir through a stem of a discharge port to establish fluid communication with a proximal end of a catheter lumen to which the port assembly is secured prior to placement of the assembly into a patient. The housing includes a base and a cap that together cooperate to secure a needle-penetrable septum within the assembly by compressing a seating flange of the septum in a seat of the housing base. The cap is mechanically secured to the housing base by a mechanical joint and solvent bonding. As in the port discussed above, the discharge port is defined by a discharge stem extending from the port assembly and is adapted to be inserted into the lumen of the proximal end of a catheter that extends into the vasculature of the patient. The discharge stem defines a pair of rounded protuberances onto which the catheter lumen wall grips tightly when the stem is fully inserted into the catheter proximal end. This is seen in FIGS. 13 and 14 hereof.

It is important to provide a venous access port assembly that provides an assured locking connection between the discharge stem and the catheter. U.S. Pat. No. 6,113,572 sets forth a connection system between a catheter's proximal end and a venous access port assembly at a discharge stem thereof. The rigid, tubular stem has a plurality of engagement barbs encircling and radially outwardly extending on an exterior surface of the stem. A compression sleeve is loosely disposed along the catheter, and the catheter's proximal end is first urged onto and over the engagement barbs, and then the compression sleeve is urged from its loose position over the catheter end fitted onto the discharge stem thus lockingly and sealingly securing the catheter to the discharge stem, in one embodiment for one type of catheter made of silicone material. For a catheter of polyurethane material, a compression sleeve is fitted onto a length of tubing larger in inner diameter than the catheter's outer diameter; when the catheter is force-fit onto the barbed discharge stem, the sleeve/tubing component is moved proximally over the catheter end, compressing the catheter lockingly and sealingly onto the discharge stem. In both embodiments, the engagement barbs have sharply defined proximal edges at their end faces against which the catheter lumen wall is firmly pressed by the locking system. The two types of connection systems are sold together with the venous access port assembly to enable the practitioner to select the appropriate one depending on the catheter selected by the practitioner.

It is desired to provide a catheter/device connection system that does not press the catheter wall directly against sharp edges of engagement barbs.

BRIEF SUMMARY OF THE INVENTION

The present invention provides a locking connection system between a catheter end and a medical device. Such system may be used with venous access port assemblies, but may also be utilized with other catheter-connecting devices such as luer fittings, hubs and tunnelers. With respect to such devices, generally a stem of each such device is force-fit into the proximal end of a flexible tube such as a catheter (or an extension tube for a catheter assembly). The present invention provides a locking component that is slid over the catheter proximal end after the catheter end has been urged over the stem. The locking component is adapted to minimize damage to the catheter lumen wall by the protuberances of the stem when the catheter lumen wall is compressed by the locking component against the stem and compressed against the protuberances of the stem. The locking component of the present invention comprises two parts that latch and lock to each other when fully urged toward each other, through at least one pair of latch arms of one of the two parts entering into latch-receiving apertures of the other part and a latching ledge of each latching arm latches to a corresponding latching ledge defined along the side wall of the latch-receiving aperture. The locking component of the present invention is utile with a stem having either barbed protuberances or rounded protuberances.

In a further aspect, for convenience of the practitioner, the two-part locking component provides first and second latching positions. The fully latched and locked position is the second position, but there is a first latching position that serves to hold the two parts together until the practitioner is ready to lock the catheter lumen to the stem. In the first position, the locking component assembly is placed onto the catheter lumen proximal end prior to urging the stem into the catheter lumen. Then the catheter lumen is force-fit onto the stem, whereafter the locking component assembly, still in its first position, is slid along the catheter until it too is disposed around the stem, with the catheter lumen wall interposed therebetween. At this point, the practitioner simply urges the two parts of the locking component assembly fully together thus locking them into the second and locked position firmly compressing the catheter lumen wall against a smaller diameter portion of the stem axially displaced from the protuberance or protuberances.

In one embodiment, the locking component is comprised of two parts that are lockable together about the catheter lumen after the lumen is force-fit over the stem. One pair of latch arms is provided to secure the first and second locking component parts to each other in a relatively open first position and a fully locked second position.

In a second embodiment, again the locking component is defined by two parts but is elongated and is provided with two pairs of latch arms and latch-receiving apertures, again defining first and second positions, a relatively open first position and a fully locked second position. The lumen-compressing surface along the inside channel of the locking component is preferably disposed axially between the two pairs of latch arms, and positioned such that the lumen-compressing surface compresses the lumen between two stem protuberances.

A method is disclosed and claimed for assuredly sealing and locking a catheter to a medical device having a stem, comprising the steps of providing a locking component for assuredly securing a catheter lumen proximal end to a stem insertable thereinto to establish a sealed fluid communication therebetween, the component having two parts securable to each other in first or open and second or fully locked positions; placing the two-part locking component along a catheter lumen proximate the proximal end thereof, urging the catheter lumen proximal end onto and around a stem; moving the locking component along the catheter until disposed over and around the stem with the catheter lumen interposed therebetween; and, urging the locking component into a fully locked position wherein the locking component compresses a portion of the catheter lumen wall firmly against the stem.

In a variation of the method described above, a method is disclosed and claimed comprising the steps of providing a locking component for assuredly securing a catheter lumen proximal end to a stem insertable thereinto to establish a sealed fluid communication therebetween, the component having two parts securable to each other in at least a fully locked position; urging the catheter lumen proximal end onto and around a stem; placing the two parts of the locking component on opposite sides of the stem, with the catheter lumen interposed therebetween; and, urging the locking component into a fully locked position wherein the locking component compresses a portion of the catheter lumen wall firmly against the stem.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 1 to 4 are of the PRIOR ART, an elevation view of a venous access port of the PRIOR ART, a cross-section thereof, and isometric views of the port with a catheter lumen positioned to be urged onto a stem of the port (FIG. 3) and with the catheter lumen urged onto the stem, with a compression sleeve generally depicted along the catheter lumen to be slid over the stem to compress the lumen against the stem;

DETAILED DESCRIPTION OF THE INVENTION

Figure 5:
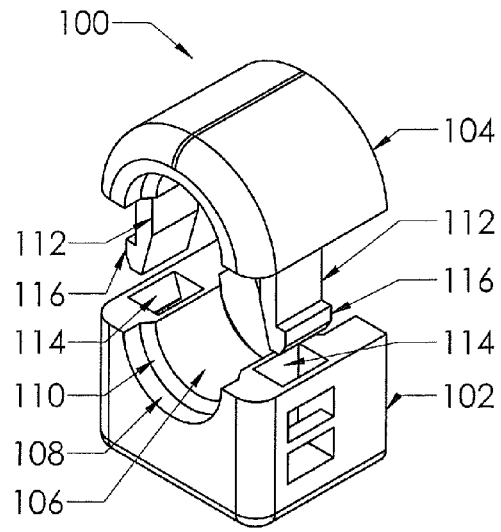
FIGS. 5 and 6 are isometric views of the a first embodiment of the locking component of the present invention with the two parts thereof positioned to be latched to each other and the fully locked together.

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of PRIOR ART FIGS. 1 to 4 includes a housing 12 and a septum 14, with a discharge port 16 extending from a distal end of the port assembly 10 to be attached securely and sealingly to the proximal end portion 32 of a catheter 30. A passageway 20 extends through the stem defining the discharge port 16 to an interior reservoir 22 that will establish fluid communication between the interior reservoir 22 and the catheter lumen 34. The stem is shown to have conventional barbed protuberances 18 onto which the catheter lumen will grip; between barbed protuberances 18 is seen a smaller diameter stem section 24. In FIG. 3, the catheter lumen is positioned and aligned with the stem 16 to be urged thereonto, with a compression sleeve 40 generally depicted along the catheter spaced from the proximal catheter end portion 32. In FIG. 4, the catheter proximal end portion has been urged onto stem 16, with expanded lumen wall sections 36 defined over the barbed protuberances; the compression sleeve may now be urged along the catheter until over and around the stem for the catheter proximal end portion to be interposed therebetween and compressed thereby onto the stem.

Figure 6:
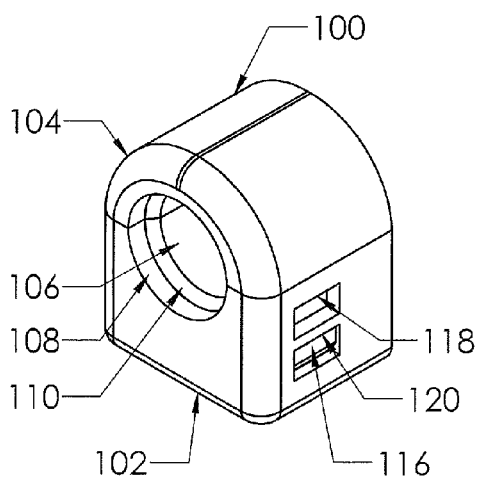
Figure 7:
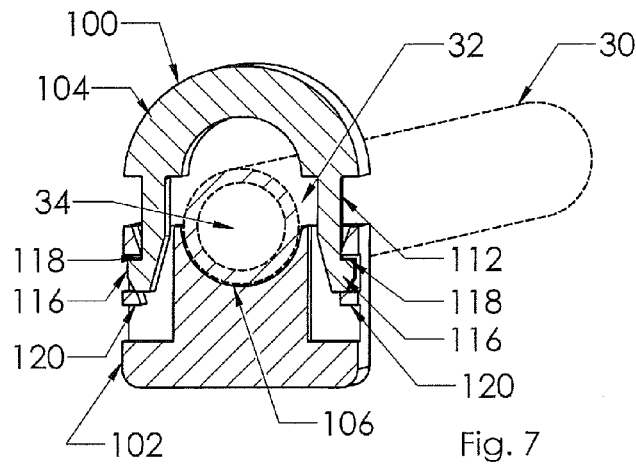
FIG. 7 is a cross-section view of the locking component of FIGS. 5 and 6 shown latched to each other in a first or partially open position, with a catheter lumen shown in phantom disposed within the channel of the locking component.

Locking component 100 of the present invention is seen in FIGS. 5 to 9. Between a lower part 102 and an upper part 104 is defined a channel 108 through which a catheter will extend, as depicted in FIG. 7. The channel 108 includes a catheter compression section 106 defined by a pair of opposed compression surfaces and that is smaller in diameter than channel 108 and is dimensioned to compress a catheter lumen when it has been inserted onto a stem of a medical device as in FIG. 4. A beveled surface 110 concludes each end of the catheter compression section 106 along the otherwise larger diameter channel 108.

Seen best in FIGS. 5 and 7, upper part 104 includes a pair of latch arms 112 depending from side portions thereof, and are aligned with latch-receiving apertures 114 into top surfaces of side walls of lower part 102 to be received thereinto, with latch arms 112 concluding in latches 116. Along side surfaces of apertures 114 are upper and lower latching ledges 118, 120 as seen in FIG. 7. Latch 116 of each latch arm can latch onto upper latching ledge 118 which defines the first or partially open position of the locking component assembly. If upper part 104 were to then be pressed further, latch 116 of each latch arm 112 will latch onto lower latching ledge 120, and this will define the second or locked position of the locking component assembly as seen in FIG. 6. Preferably, the upper and lower latching ledges 118,120 both extend through the sidewalls to the exterior, for ease of manufacture. In FIG. 7, it is seen that locking component 100 has been manipulated to its first or partially open state and placed along catheter 30, with latches 116 latched onto upper latching ledges 118.

Figure 8:
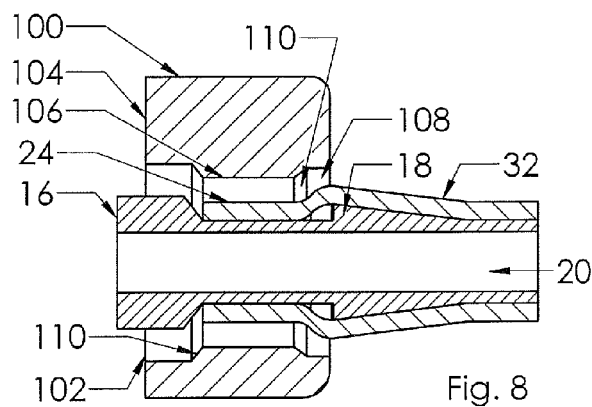
FIGS. 8 and 9 are longitudinal cross-sections of the locking component of FIGS. 5 to 7, with the locking component in a first or partially open position (as in FIG. 7) shown about a stem of the port of FIGS. 1 to 4, having the catheter lumen urged onto and around the stem, and with the locking component urged to its second and locked position compressing the catheter lumen against the stem axially spaced from a barbed protuberance of the stem.
Figure 9:
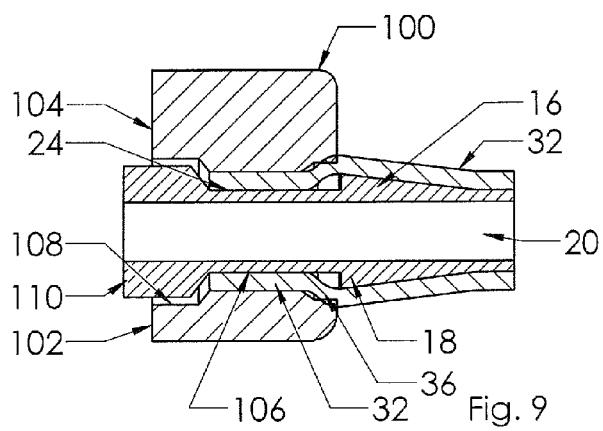

Now referring to FIGS. 8 and 9, a stem 16 of a port such as port 10 of FIGS. 1 to 4 is seen to have at least one barbed protuberance, and a recessed area to the left in FIGS. 8 and 9 where the stem has a smaller diameter section 24. A proximal end portion 32 of a catheter 30 has been urged onto stem 16 in both figures. Locking component 100 has been moved along catheter 30 to its proximal end 32 and is situated around stem 16, still in its first partially open position in FIG. 8. Compression surface 106 is seen to be poised about the smaller diameter section 24 of the stem to the left of the barbed protuberance 18 and about the proximal end of catheter 30. In FIG. 9, locking component 100 has been pressed together into its second and locked position, with its compression surface 106 compressing catheter proximal end 32 against the smaller diameter section 24 of the stem. Clearly seen in FIGS. 8 and 9, beveled surfaces 110 are axially spaced from the barbed protuberance, and compression surface 106 is not compressing any portion of the catheter lumen wall against the barbed protuberance, nor is any portion of the larger diameter channel portions 108 of locking component 100, thus preventing any damage to the catheter lumen wall by means of the locking component.

Figure 13:
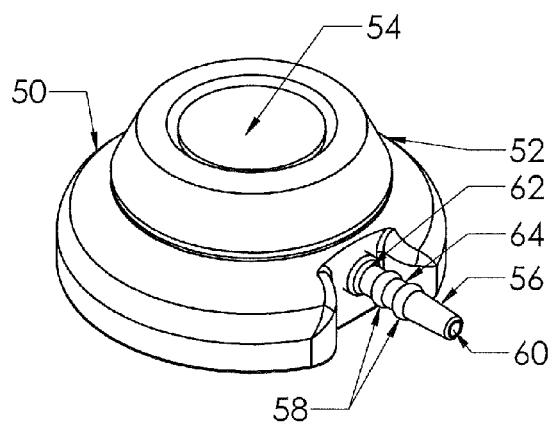
FIGS. 13 and 14 show a port in isometric view and an enlarged cross-sectional view of a stem of the port having rounded protuberances.
Figure 14:
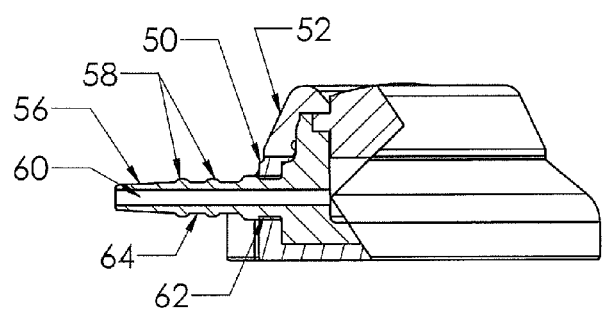

A second embodiment of locking component 200 is depicted in FIGS. 10 to 12, 15 and 16. A second stem design 56, with rounded annular protuberances 58 separated by a smaller diameter section 64, appears in FIGS. 13 to 16, part of a different design of venous access port 50 of FIGS. 13 and 14. Port 50 and its stem 56 are of the type disclosed in U.S. Patent Publication No. US 2007/0270770 and discussed in the Background hereof. Locking component 200 again has an upper part 204 and a lower part 202, a channel 208, a compression surface 206 of smaller diameter than the remainder of channel 208. Two pairs of latch arms 212 depend from upper part 204 aligned with latch-receiving apertures 214 of lower part 202, and latch arms 212 conclude in latch sections 216 that latch in cooperation with upper and lower latching ledges along side surfaces of apertures 214, in similar fashion to locking component 100 of FIGS. 5 to 9, to define first partially open and second locked positions of the locking component assembly, seen respectively in FIGS. 12 and 11. The latching ledges can be the upper surfaces of upper and lower sidewall openings 218,220 of lower part 202. A proximal end 222 of locking component 200 can be seen to be larger in outer and inner diameter than distal end 224 thereof proximal end 220 is larger to accommodate the larger dimensioned portion 62 of stem 56 as it joins to the port 50 (FIG. 14).

Figure 15:
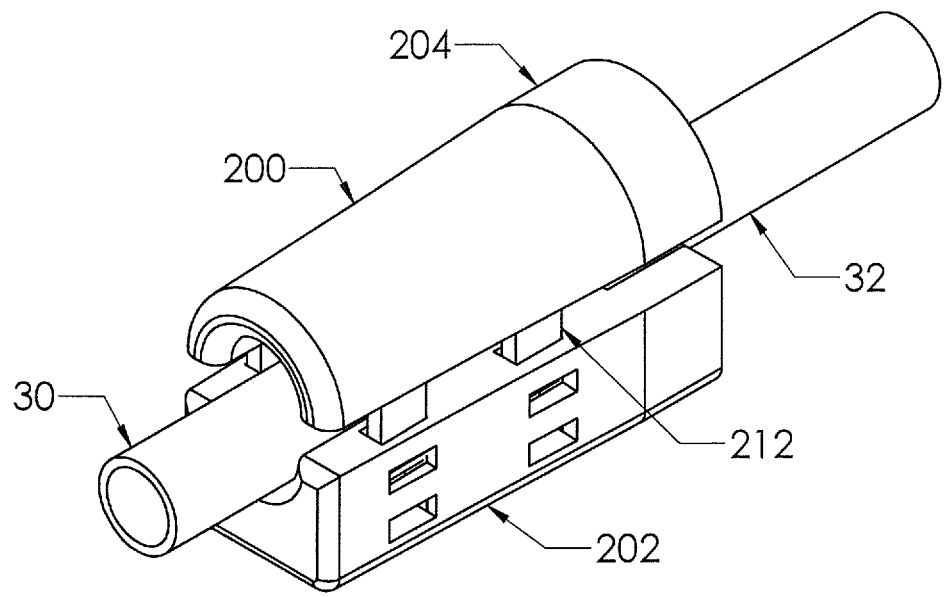
FIGS. 15 and 16 show the port of FIGS. 13 and 14 and a catheter lumen being assembled thereto with the locking component embodiment of FIGS. 10 to 12 being assembled thereto.
Figure 16:
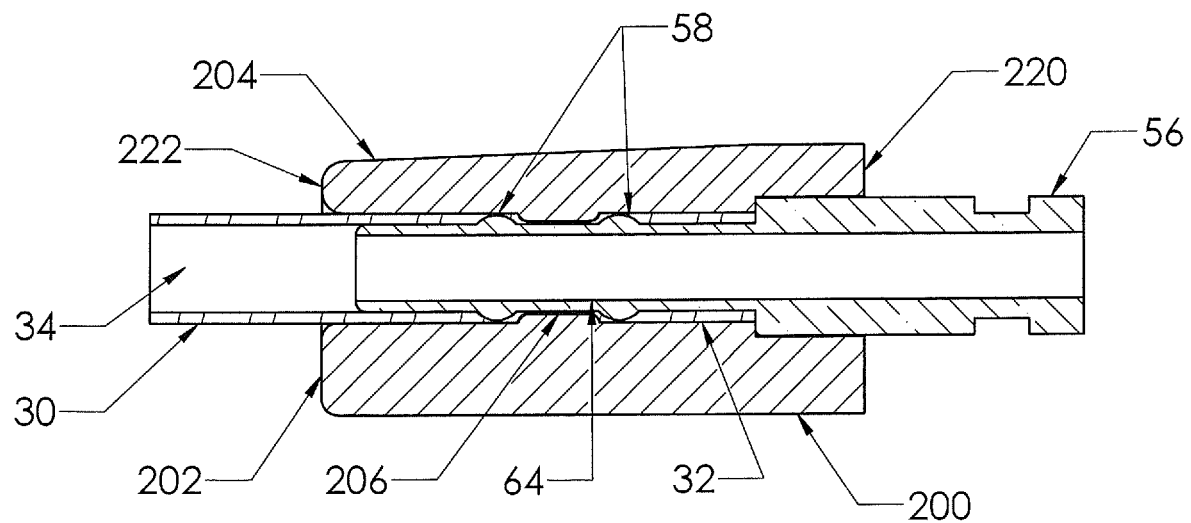

Locking component 200 is shown in FIG. 15 to be pre-assembled in its first partially open position and placed along a catheter 30 near to proximal end 32. FIG. 16 illustrates that catheter proximal end 32 has been urged onto stem 56 (FIGS. 3 and 14). Locking component 200 has been moved into position at the catheter proximal end and around the stem, and it has been manipulated by the practitioner into its second locked position, clamping the catheter lumen against the stem by means of compression surface 206 which is disposed in alignment with smaller diameter stem section 64 axially between rounded protuberances 58. Again, as with locking component 100, compression of the catheter lumen wall by the locking component does not directly squeeze any portion of the catheter lumen wall against the protuberances thus preventing damage to the catheter lumen by the locking component.

Figure 10:
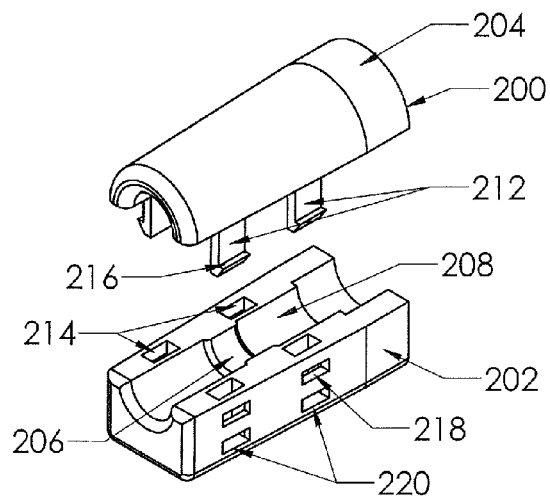
FIGS. 10 to 12 are isometric views of a second embodiment of locking component of the present invention with the two parts separated from each other, fully locked to each other, and latched to each other in a first and partially open position.
Figure 11:
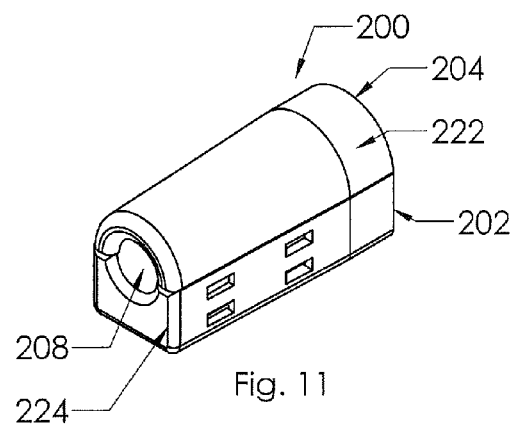
Figure 12:
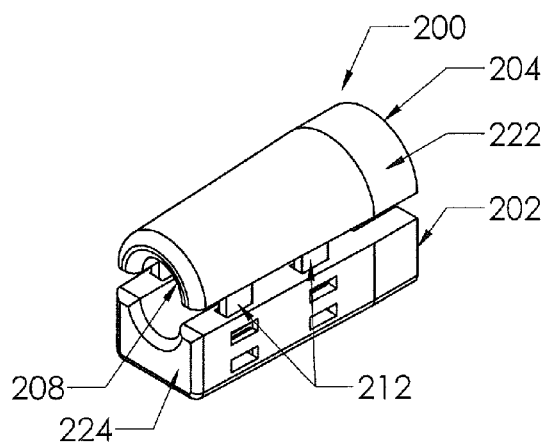
Figure 17:
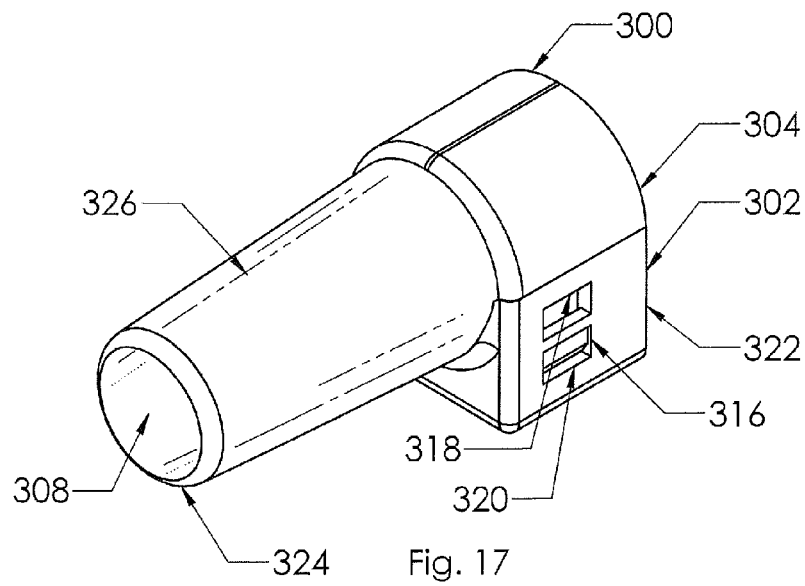
FIGS. 17 to 19 illustrate a third embodiment of the locking component of the present invention.
Figure 18:
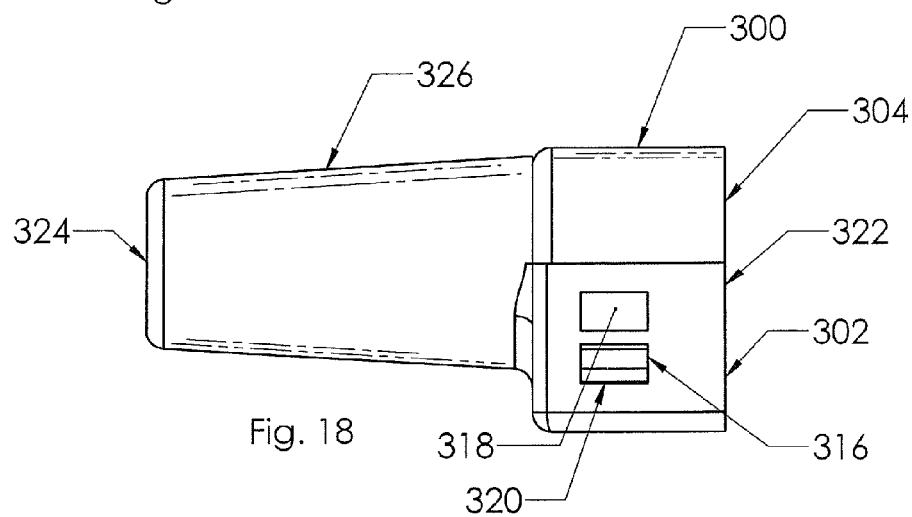
Figure 19:
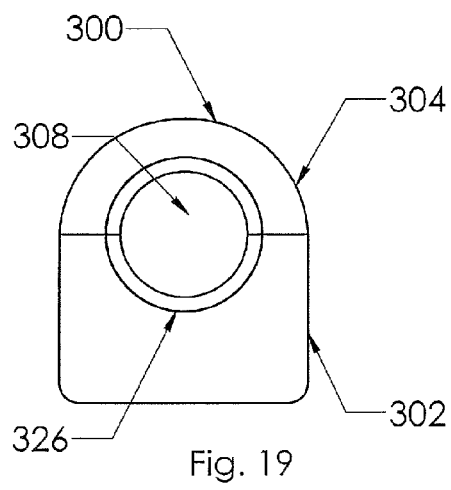
Figure 20:
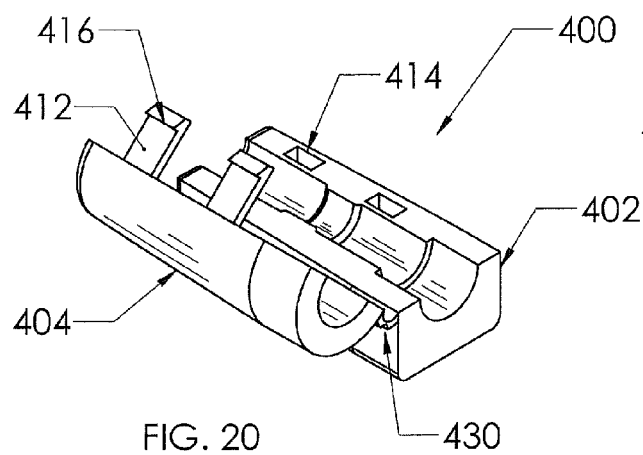
FIGS. 20 to 23 illustrate a fourth embodiment of locking component, wherein upper and lower sections are joined by a living hinge.
Figure 21:
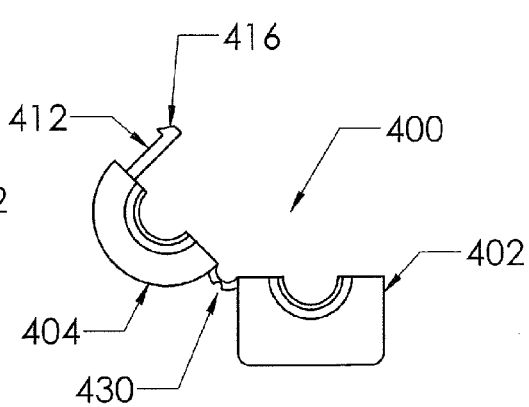
Figure 22:
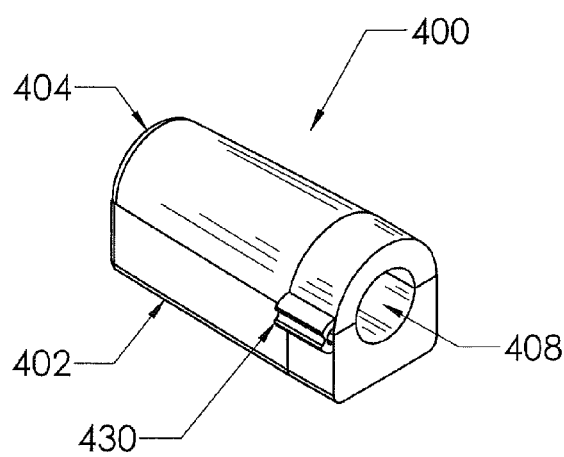
Figure 23:
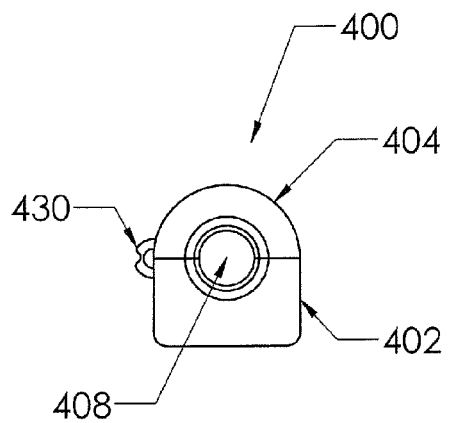

Locking component 300 is shown in FIGS. 17 to 19, having upper and lower sections 302,304; a frustoconical portion 326 extending distally or away from the port to which the catheter is to be assembled (not shown); and a catheter passageway 308 extending from distal end 324 to proximal end 322. Lower section 302 includes pairs of upper and lower latching ledges 318,320 and upper section 304 includes a pair of legs having latches at free ends thereof cooperable with the ledges to secure the upper and lower sections to each other about the catheter in both a pre-assembled position and fully locked position once the catheter proximal end is urged onto the port stem, similar to those of locking component 100 of FIGS. 10 to 12. Alternatively, the lower section could provide a pair of upper latch apertures, as is illustrated in FIGS. 10 to 12. Frustoconical distal portion 326 can preferably be defined by the lower section and has a more atraumatic shape extending along the catheter.

In another embodiment illustrated in FIGS. 20 to 23, the locking component 400 can comprise upper and lower portions 404,402 defining catheter passageway 408 therebetween, that are joined to each other along one side by a living hinge 430 (or more than one), with latch arms 412,416 and apertures 414 or other latching arrangement defined along the other side to enable the upper and lower portions to be manipulated into at least a locked position.

It has been discussed hereinabove that the locking component of the present invention is conveniently shipped in its pre-assembled state which is the first partially open position, enabling easy placement by the practitioner onto the catheter proximal end during catheter implantation into a patient. Then, when the catheter proximal end has been urged onto the stem of the port or other medical device, the locking component can easily be slid along the catheter and into position adjacent to the port or medical device, surrounding the stem with the catheter proximal end portion interposed therebetween, after which the practitioner can easily press the upper and lower parts of the locking component together into the second locked position, establishing an assured catheter locked connection to the medical device. However, it is within the scope of the claims and the spirit of the invention for the locking component to be used as separate upper and lower parts that are urged directly onto the catheter proximal end after it has been urged onto the stem, in which case only one position, the locked position is necessary to be defined by the locking component. The present invention has been shown to be useful with stems having either the conventional barbed protuberances or having rounded protuberances. The locking component preferably has all outer edges and corners rounded and atraumatic. The locking component can be provided in a kit with the catheter and the venous access port or other medical device, enabling appropriately complementary geometry and dimensions. The locking component can be made of, for example, polycarbonate. The locking component can be utilized with catheters that are of various materials such as silicone or polyurethane, for example.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A catheter locking component for assuredly locking a catheter onto a stem of a medical device, the stem comprising at least one protuberance, comprising:
    an upper part comprising an upper sidewall comprising:
        an upper semi-cylindrical compression surface;
        a first side portion attached to a first latch via a first latching arm depending from the first side portion; and
        a second side portion attached to a second latch via a second latching arm depending from the second side portion; and
    a lower part comprising:
        a lower semi-cylindrical compression surface;
        a first sidewall comprising:
            a first top surface;
            a first aperture formed in the first top surface and aligned with the first latch;
            a first upper opening to the first aperture in the first sidewall forming a first upper latching ledge; and
            a first lower opening to the first aperture in the first sidewall forming a first lower latching ledge; and
        a second sidewall comprising:
            a second top surface;
            a second aperture formed in the second top surface and aligned with the second latch;
            a second upper opening to the second aperture in the second sidewall forming a second upper latching ledge; and
            a second lower opening to the second aperture in the second sidewall forming a second lower latching ledge,
    wherein the first aperture is configured to receive the first latch, and the second aperture is configured to receive the second latch,
    wherein the upper and lower parts are in a first position when the first latch is engaged with the first upper latching ledge and the second latch is engaged with the second upper latching ledge, and
    wherein the upper and lower parts are in a second position when the first latch is engaged with the first lower latching ledge and the second latch is engaged with the second lower latching ledge, the first and second semi-cylindrical compression surfaces forming a catheter compression section configured to compress the catheter against the stem at a location axially spaced from the at least one protuberance.

2. The locking component of claim 1, wherein a diameter of the compression section is smaller than the greatest outer dimension of the protuberance of the stem, when the upper and lower parts are in the second position.

3. The locking component of claim 1, wherein the upper part further comprises an upper semi-cylindrical channel in which the upper semi-cylindrical compression surface is disposed and the lower part further comprises a lower semi-cylindrical channel in which the lower semi-cylindrical compression surface is disposed, the upper and lower semi-cylindrical channels forming a channel comprising a diameter greater at a first end of the channel than at a second end of the channel.

4. The locking component of claim 1, wherein, when the upper and lower parts are in the second position, all outer corners and edges of the locking component are rounded.

5. The locking component of claim 1, wherein the assembly includes a frustoconical section extending distally along the catheter upon assembly.

6. The locking component of claim 1, wherein the first upper latching ledge and the first lower latching ledge extend to an outer surface of the first sidewall, and the second upper latching ledge and the second lower latching ledge extend to an outer surface of the second sidewall.

7. The locking component of claim 1, wherein:
    the first and second latches form a first pair of latches,
    the upper part further comprises a further latch attached to the first side portion via a further latching arm depending from the first side portion and a further latch attached to the second side portion via a further latching arm depending from the second side portion, the further latches forming a second pair of latches, and
    the second pair of latches are receivable into respective further latch-receiving apertures in the first and second top surfaces of the lower part.

8. The locking component of claim 7,
    wherein the first pair of latches are spaced apart from the second pair of latches axially, and
    wherein the semi-cylindrical upper compression surface is disposed between the first and second pair of latches.

9. The locking component of claim 1, wherein, when the upper and lower parts are in the first position, the locking component is adapted to be moved along the catheter to an end of the catheter that is inserted over the stem, and the upper and lower semi-cylindrical compression surfaces are sufficiently spaced apart to pass over the at least one protuberance when the catheter has been inserted over the at least one protuberance.

10. A method for connecting a catheter onto a stem of a medical device, the stem comprising at least one protuberance, the method comprising steps of:
    urging a proximal end of the catheter onto the stem of the medical device to dispose the proximal end of the catheter over the at least one protuberance of the stem;
    placing a locking component about the stem, the locking component comprising:
        an upper part comprising an upper sidewall comprising:
            an upper semi-cylindrical compression surface;
            a first side portion attached to a first latch via a first latching arm depending from the first side portion; and a second side portion attached to a second latch via a second latching arm depending from the second side portion; and
a lower part comprising:
a lower semi-cylindrical compression surface;
a first sidewall comprising:
a first top surface;
a first aperture formed in the first top surface and aligned with the first latch;
a first upper opening to the first aperture in the first sidewall forming a first upper latching ledge; and
a first lower opening to the first aperture in the first sidewall forming a first lower latching ledge; and
a second sidewall comprising:
a second top surface;
a second aperture formed in the second top surface and aligned with the second latch;
a second upper opening to the second aperture in the second sidewall forming a second upper latching ledge; and
a second lower opening to the second aperture in the second sidewall forming a second lower latching ledge,
wherein the first aperture is configured to receive the first latch, and the second aperture is configured to receive the second latch; and
manipulating the locking component from a partially open position to a locked position in which the locking component compresses the catheter against the stem,
wherein, in the partially open position, the first latch is engaged with the first upper latching ledge and the second latch is engaged with the second upper latching ledge, and
wherein in the locked position, the first latch is engaged with the first lower latching ledge and the second latch is engaged with the second lower latching ledge, the first and second semi-cylindrical compression surfaces thereby forming a catheter compression section that compresses the catheter against the stem at a location axially spaced from the at least one protuberance.

11. The method of claim 10, wherein the step of placing is performed prior to the step of urging.

12. The method of claim 10, wherein the step of placing comprises sliding the locking component along the catheter and into position over the proximal end of the catheter.

13. The method of claim 10, wherein the step of placing the locking component about the stem comprises a step of assembling the locking component directly around the stem having the catheter urged thereonto.

14. The method of claim 13, wherein the step of assembling the locking component directly around the stem includes a step of assembling the locking component into the partially open position such that the locking component remains assembled around the catheter urged onto the stem.

15. The method of claim 10, further comprising providing the locking component in a kit in which the locking component is pre-assembled in the partially open position.

* * * * *